(12) United States Patent
Vakina et al.

(10) Patent No.: US 9,730,973 B2
(45) Date of Patent: Aug. 15, 2017

(54) METHOD FOR RESTORING MALE SEX DRIVE (LIBIDO)

(71) Applicant: OBSCHESTVO S ORGANICHENNOJ OTVETSTVENNOST'JU "PARAFARM", Penza (RU)

(72) Inventors: Tatiana Nikolaevna Vakina, Penza (RU); Elena Vladimirovna Petrova, Penza (RU); Viacheslav Nicolaevich Trifonov, Zarechny (RU); Evgenij Nikolaevich Krutiakov, Penza (RU); Aleksandr Viktorovich Fedorov, Kuznetsk (RU); Elena Stanislavovna Andreeva, Penza (RU); Tatiana Viktorovna Elistratova, Penza (RU); Irina Vladimirovna Khomykova, Penza (RU); Galina Anatolievna Tolbina, Penza (RU)

( * ) Notice: Subject to any disclaimer, the term of this patent is extended or adjusted under 35 U.S.C. 154(b) by 102 days.

(21) Appl. No.: 14/422,206

(22) PCT Filed: Mar. 6, 2013

(86) PCT No.: PCT/RU2013/000173
§ 371 (c)(1),
(2) Date: Feb. 18, 2015

(87) PCT Pub. No.: WO2014/031026
PCT Pub. Date: Feb. 27, 2014

(65) Prior Publication Data
US 2015/0231189 A1 Aug. 20, 2015

(30) Foreign Application Priority Data
Aug. 20, 2012 (RU) ................. 2012135560

(51) Int. Cl.
| | | |
|---|---|---|
| A61K 36/00 | (2006.01) |
| A61K 36/296 | (2006.01) |
| A61K 31/198 | (2006.01) |
| A61K 31/7048 | (2006.01) |
| A61K 31/20 | (2006.01) |
| A61K 31/315 | (2006.01) |
| A61K 31/675 | (2006.01) |
| A61K 36/258 | (2006.01) |
| A61K 35/64 | (2015.01) |

(52) U.S. Cl.
CPC .......... *A61K 36/296* (2013.01); *A61K 31/198* (2013.01); *A61K 31/20* (2013.01); *A61K 31/315* (2013.01); *A61K 31/675* (2013.01); *A61K 31/7048* (2013.01); *A61K 35/64* (2013.01); *A61K 36/258* (2013.01)

(58) Field of Classification Search
None
See application file for complete search history.

*Primary Examiner* — Qiuwen Mi
(74) *Attorney, Agent, or Firm* — Patentagar PLLC; Alexander Rabinovich

(57) ABSTRACT

The method for restoring male sex drive (libido) using a food supplement for restoring male sex drive (libido) relates to medicine, and more specifically to the pharmaceutical industry producing food supplements for restoring male sex drive (libido) and male sexual function which are based on natural ingredients. The method involves the use of nitric oxide (NO) in terms of L-arginine, pollen or beebread in terms of rutin, drone brood in terms of decenoic acids, a substance containing zinc in terms of zinc, a substance containing vitamin B6 in terms of vitamin B6, horny goat weed in terms of icariin, true or false *ginseng* root in terms of saponins, and *leuzea* or crowned saw-wort in terms of ecdysteroids, in various combinations.

7 Claims, No Drawings

METHOD FOR RESTORING MALE SEX DRIVE (LIBIDO)

CROSS REFERENCE TO RELATED APPLICATIONS

This application is a national stage entry of PCT/RU2013/000173, filed Mar. 6, 2013, which published as WO 2014/031026 on Feb. 27, 2014, in a language other than English, which claims priority to RU Application No. 2012135560, filed Aug. 20, 2012.

The invention relates to medicine, namely the pharmaceutical industry, which produces biologically active food supplements to restore sex drive (libido) and improve sexual function in male and is based on natural ingredients.

Sexual dysfunction, including decreased libido, erectile and ejaculation dysfunction, as well as infertility, are widespread medical, psychological, and social problems.

Today there are a large number of drugs for sexual dysfunction treatment—pharmacological group—inhibitors of phosphodiesterase of type 5 (PDEI-5: Viagra, Cialis, Zidena, Levitra). At the same time, the high cost of these drugs and significant risk of adverse drug reactions, especially in patients with cardiovascular disease, limit their widespread use. In addition, there are patients (15-42%) in which PDE5 inhibitors are inefficient due to the mechanism of action of this group of drugs. It is known that these drugs can potentiate NO relaxing action on smooth muscle tissue of trabecular cells. However, the starting point for NO release from nerve endings is the impulses coming from the central nervous system. Their intensity depends on the patient's response to sexual stimuli, i.e. intensity of sex drive or libido. With a sharp decrease of libido, namely it fades with age; monotherapy with PDE5 inhibitors is ineffective due to lack of substrate for their actions (Segraves K B, Segraves R T., 1991; Pushkar D. Y., Yudovsky S. O., 2007).

As for androgen replacement therapy (ART: testosterone agents per os, intramuscular, transdermal), despite the variety of dosage forms there is a number of unresolved problems. Firstly, none of the drugs is able to precisely reproduce a circadian rhythm in serum testosterone levels. Secondly, a number of studies have shown that exogenous increase of testosterone has a greater influence on erectile function rather than sexual-erotic, libidinal component that is associated with initial defect of hypothalamic brain structures. Third, androgens can potentially have adverse effects not only due to cut off its own mechanisms of androgen production but also affecting systems of homeostasis maintaining that inhibit the production of endogenous androsteroids. Side effects primarily affect the prostate gland, lipid profile, cardiovascular system, hematological, sleep system, social behavior, and emotional status (Pushkar D. Y., Segal A. S., Yudovsky S. O., 2008). In case of ART one should ensure the functional safety of the liver to avoid final catabolism disorders with increased levels of estrogen that provokes release of inhibiting substances able to block achievable, usually modest, positive therapeutic results.

Impaza—medicine containing antibodies to human endothelial NO-synthase. The main mechanism of its action is to increase the activity of endothelial NO-synthase, recovery of endothelium nitric oxide (NO), increase of cGMP content in smooth muscles and its relaxation that leads to an increase of blood supply to the corpus cavernosum. These effects primarily recover erection. With regard to the libido target studies have not been conducted; according to individual data increase of libido is less than 20% (Neumark A. I., Simashkevich A. V., Aliyev R. T. et al., 2010).

The closest analogue to the proposed drug are formulations that are useful in the treatment of male and female impotence; they are based on extracts of Tribulus terrestris, Epimedium koreanum and Cinnamon cassia, combined in a specific weight ratio and optionally contain arginine or physiologically equivalent ester, salt or precursor and suitable carrier or excipient (patent of the Russian Federation No 2313358, 2003).

The effect of this composition on libido is low. This drug is primarily aimed at the elimination of erectile dysfunction. Another disadvantage of this drug is the use of a medicinal plant Tribulus terrestris, which is prohibited by Rospotrebnadzor of RUSSIA (Russian Federal Service for Surveillance on Consumer Rights Protection and Human Wellbeing) for use as a raw material for the production of biologically active additives to food because of the high toxicity of this plant.

We offer a remedy to restore/enhance libido with the next composition of the daily dosage with limited range:

| Components | Mg of active substance |
| --- | --- |
| True or false *ginseng* root in terms of saponins | from 5 mg to 20 mg |
| *Leuzea* root in terms of ecdysteroids | from 0.1 mg to 30 mg |
| L-Arginine | From 300 mg to 1,000 mg |
| Horny goat weed in terms of icariin | From 20 to 150 mg |
| Male bee brood in terms of decenoic acid | from 0.4 mg to 1 mg |
| Pollen or beebread in terms of rutin | from 40 mg to 100 mg |
| Zinc citrate in terms of zinc | from 6 mg to 60 mg |
| Vitamin B6 | from 0.3 mg to 3 mg |

The upper limit is due to toxicity, the lower limit-effectiveness.

L-Arginine is a protein-forming amino acid. It is a source of adequate forming of nitric oxide (NO) by vascular endothelium, which is associated with the dependent relaxation of smooth muscle cells of cavernous tissue determining the hemodynamic changes in the penis during erection and rigidity phase (K. E. Anderson, 2001). L-arginine has stimulating effect on the reproductive system: it increases the production of seminal fluid, spermatogenesis; stimulates the potency and sexual activity; can increase the strength and duration of blood supply to the genitals; prolongs the time of sexual intercourse; enhances pleasant sexual sensations; makes orgasms last longer; increases the frequency and intensity of orgasms. It improves mood, activity and endurance.

Horny Goat Weed contains icariin~flavone derived from plants of Epimedium family, which are widely known as Horny Goat Weed (literally—herb of horny goat). The extract of Epimedium for centuries has been used to treat impotence and improve sexual function in Chinese traditional medicine.

The mechanism of action is similar to a phosphodiesterase inhibitor. It increases the production of nitric oxide, improves circulation and muscle power. It is tropic to androgen receptors and acts like testosterone, causing accelerated growth of muscle tissue, increases sex drive and endurance. Horny Goat Weed extract has antioxidant, anti depressive and neuroprotective effects.

Male bee brood (male bee-brood homogenate) is a natural substance which contains natural testosteroids, progesterone and estradiol. Male bee brood restores metabolism and nutrition of tissues, helps to stabilize blood pressure, has a regulating effect on the tone of the vascular system and the level of blood circulation, lowers blood cholesterol levels. It promotes the accelerated recovery and biochemical and mass-metric characteristics of testes and prostate. As a stimulant of the central mechanisms of regulation of androgens formation, it increases physical performance, helps to restore impaired sexual function in males and increases sexual desire.

Pollen or beebread is male plant cells, natural concentrate containing proteins, all essential amino acids, carbohydrates, lipids, minerals and microelements (potassium, calcium, phosphorus, ferrum, magnesium, manganese, chromium, zinc, iodine, etc.), vitamins (carotenoids, C, D, E and group B, P, PP, K et al.), phytohormones and flavonoids. Pollen restores liver function; lowers the level of blood sugar; normalizes the process of digestion; stimulates the adrenal glands; lowers blood cholesterol; normalizes blood pressure; increases stress resistance, mental and physical performance. It enhances male potency and reduces the signs of prostatic hypertrophy.

Zinc citrate—zinc has a strong immunostimulatory effect. It actively influences the state of the sexual function of men: it is building blocks of testosterone; it increases activity of sperm, promotes proper functioning of male sex glands. Zinc deficiency plays a key role in the development of benign prostatic hyperplasia (adenoma) (BPH). Thus, the activation of enzyme 5-alpha-reductase occurs, which converts testosterone into dehydrotestosterone (DHT). Testosterone levels in the blood decreases, DHT accumulates in the prostate gland which leads to prostate enlargement. A high content of zinc contributes to this process blocking. It has psychotropic (improves mood, reduces irritability, improves memory and attention) and antioxidant actions.

Vitamin B6 normalizes hormonal balance, improves the immune system, heart function, restores the function of prostate cells. It plays an important role in the treatment of infertility and energy processes occurring in spermatozoa, especially in reducing their mobility.

True or false *ginseng* root has adaptogenic, bio-stimulating, and tonic effects. Pharmacological activity is due to the content of saponin glycosides and ginsenosides, fatty ester oils, sterols, peptides, vitamins and minerals. The active ingredients of *ginseng* improve prostate function and sexual activity, actively influence the central nervous system, increase working capacity, and reduce physical and mental fatigue. In addition, *ginseng* improves the functional activity of cardiovascular system and regulates blood pressure.

*Leuzea* root has tonic and stimulant properties. The main pharmacological properties are the increase of muscle contraction and performance, improvement of blood supply to the muscles and brain. In case of long administration it reduces morbidity, improves self-reported health, increases static endurance, improves mental and physical performance.

As one could see from the proposed composition none of the proposed components has a pronounced effect on libido increase. Any two, three, four or five components of the proposed agent do not increase libido.

During the investigations it was established that only the combination of said means and only in this range can significantly increase libido within 20-43%. I.e. studies revealed features sufficient to produce the desired synergistic effect.

Increasing libido even by 20% is significant as not all known drugs that increase sexual activity can increase libido up to even by 20%.

Libido level is a determining factor in male sexual activity, potency preservation, physiological and mental health.

In the study of "Remedy 1" significant improvement of neurohormonal and mental components of male copulative cycle was revealed resulting in enhancement/restore of libido and overall satisfaction with sexual intercourse in the studied males.

A positive correlation between the increase of blood levels of androgens (total testosterone and dehydroepiandrosterone sulfate) and a significant libido (42.8%) in men was established which indicates the presence of the drugcentral hypothalamic-pituitary mechanism of action. It is assumed that androgens increase desire by increasing the sensitivity of the pleasure centers in the limbic system and hypothalamus, as well as by increasing overall activity and vitality of the body due to the stimulating effect of androgens on metabolism.

The central mechanism of action of the drug is confirmed by the decrease of prolactin level in blood serum (548±136 to 24.5-467 mU/l, p<0.02) and the expression of anti-stress, psycho-stabilizing effects, as well as increase of libido, sexual activity due to stimulating action of LH on Leydig cells secreting testosterone.

Claimed remedy has powder, tableted or encapsulated forms and may also have a form of hydroalcoholic extract and forms based on this extract, namely, powder, tablets and capsules.

Examples of food supplements preparations.

EXAMPLE 1

For 1000 packaging products in capsules of 0.5 g with 100 capsules per pack it is taken a mixture of 50 kg of:
Powdered:
Pollen—5000 g
L-arginine—15000 g
Male bee-brood homogenate—5000 g
Zinc citrate—1000 g
Icariin (Horny Goat Weed extract)—5000 g
Vitamin B6—30 g
True Ginseng root—4500 g
*Leuzea* root—2500 g
Fillers (lactose)—11970 g
The mixture is stirred in a mixer for 3 hours; then it is encapsulated in a known manner.

EXAMPLE 2

For 2000 packaging products in tablets of 0.5 g with 100 tablets per pack it is taken a mixture of 100 kg of:
Powdered:
Pollen—10000 g
L-arginine—30000 g
Male bee-brood homogenate—10000 g
Zinc citrate—2000 g
Icariin (Horny Goat Weed extract)—10000 g
Vitamin B6—60 g
True Ginseng root—9000 g
*Leuzea* root—5000 g
Fillers (lactose)—23940 g
The mixture is stirred in a mixer for 3 hours; then it is tableted in a known manner.

This technical result is confirmed by researches conducted in the "Secrets of Longevity" medical center in Penza, which showed high efficiency of the claimed remedy compared to control groups for libido increase.

For the first study we prepared six-component food supplements based on Horny Goat Weed—remedy 1 and *Leuzea*—Remedy 2

The following compounds in a daily dosage were suggested for study:

Contents of Plant Components in the "Remedy 1"

| Components | mg |
|---|---|
| L-arginine | 900 |
| Horny Goat Weed in terms of icariin | 60 |
| Male bee brood in terms of decenoic acid | 1 |
| Pollen or beebread in terms of rutin | 48 |
| Zinc citrate in terms of zinc | 9 |
| Vitamin B6 | 1.8 |

Contents of Plant Components in the "Remedy 2"

| Components | mg |
|---|---|
| L-arginine | 900 |
| Leuzea root in terms of ecdysteroids | 0.15 |
| Male bee brood in terms of decenoic acid | 1 |
| Pollen or beebread in terms of rutin | 48 |
| Zinc citrate in terms of zinc | 9 |
| Vitamin B6 | 1.8 |

The study investigated the clinical features of psychogenic erectile disorders and noted mental disorders, the efficacy of "Remedy 1" and "Remedy 2" on the dynamics of sexual function by blood testosterone levels, sexual activity parameters (libido and erection) and psychic emotional status in patients with erectile dysfunction; therapeutic dynamics of remedies was compared.

A clinical study was conducted in 30 men with erectile dysfunction. Inclusion criteria were:

19-60 years old (age limit was associated with frequent detection in men older than 60 years of the severe cerebral organic and physical illnesses and involution processes);

matching of patient's condition at the time of inclusion to diagnostic criteria of ICD 10 B 52.2—absence of genital response, accompanied by one of the following neurotic disorders: anxiety-phobic (F40); mixed anxiety-depressive disorder (F41.2) and adaptation disorder (F 43.2);

absence of leading organic lesion in pathogenesis of sexual disorder.

The study did not include patients with alcoholism; drug addiction; anatomical deformity of the penis; proven endocrine causes of ED; decompensated somatic diseases; use other treatment agents for ED and drugs that can cause ED. All patients gave informed consent to participate in the study.

To achieve the objectives of the study, patients by simple randomization technique were divided into 3 treatment groups—two experimental and one control:

Group 1. Experimental group—12 people with erectile dysfunction and combined psychoemotional disorders receiving "Remedy 1" and the traditional psychopharmacotherapy.

Group 2. Experimental group—13 people with erectile dysfunction and combined psychoemotional disorders receiving "Remedy 2" and traditional psychopharmacotherapy.

Group 3. Control group—5 people with erectile dysfunction and combined psychoemotional disorders receiving traditional psychopharmacotherapy.

During clinical and sexual examination extent and dynamics of sexual pathological symptoms during therapy were evaluated by the clinical questionnaire "Sexual Formula for Men" (SFM) and sexual function state questionnaire (Vakina T N 2001).

Laboratory and instrumental examination included complete blood count, urinalysis, hormonal status examination—level of total serum testosterone, as well as transrectal prostate ultrasound. Consultative examination by urologist was performed.

The mental state of the patients was determined by clinical and psychopathological method. Examination of personality characteristics was performed by Mini-Mult questionnaire. Intensity and dynamics of anxiety-depressive disorder symptoms during therapy were evaluated by Hospital Anxiety and Depression Scale (NADS).

Registration of side effects was conducted on UKU scale with the date of their onset and end.

The scheme of examination is presented in Table 1. Within 4 weeks "Remedy 1" and "Remedy 2" were administrated within daily dose 2 times a day 30 minutes before meal. Evaluation of the results of therapy was performed on the 28th day of treatment. The main criterion of efficacy was the recovery of sexual activity.

TABLE 1

Scheme of patients examination

| Documents and research methods | Stage I (enrollment in the study) Screening and randomization (days 0-7) | Stage II (drug therapy) Days of treatment | | | | |
|---|---|---|---|---|---|---|
| | | 3 | 7 | 14 | 21 | 28 |
| Informed consent for participation in the study | V | — | — | — | — | — |
| CRFs | V | V | V | V | V | V |
| SFM questionnaire | V | — | — | — | — | V |
| State of sexual function questionnaire (Vakina TN 2001) | V | — | — | — | — | V |
| Level of total serum testosterone | V | — | — | — | — | V |
| HADS scale | V | — | — | — | — | V |
| Mini-Mult questionnaire | V | — | — | — | — | — |
| TRUS of prostate | V | — | — | — | — | — |
| Consultation of urologist | V | — | — | — | — | — |
| Blood and urine tests | V | — | — | — | — | — |
| Evaluation of side effects | — | V | V | V | V | V |

Study results were processed using the statistical program "STATISTICA-6.0".

All 30 patients completed the study. Characteristics of patients with erectile dysfunction included in the study are presented in Table 2.

TABLE 2

Characteristics of study patients with erectile dysfunction (n = 30)

| Values | Patients treated by remedy 1 (n - 12) | Patients treated by remedy 2 (n = 13) | Patients of control group (n = 5) |
|---|---|---|---|
| Age (average value) | 49.6 ± 6.9 | 47.3 ± 5.9 | 47.3 ± 5.1 |
| Family status | | | |
| Single | — | 4.8% | — |
| Married | 83.4% | 80.9% | 80.0% |
| Divorced | 8.3% | 4.8% | — |
| Civil marriage | 8.3% | 9.5% | 20.0% |
| Level of education | | | |
| Higher | 58.3% | 57.2% | 60% |
| Secondary professional | 16.7% | 19.0% | 20% |
| Secondary | 25.0% | 23.8% | 20% |
| Anthropometric parameters | | | |
| Trochanteric index | 1.9 ± 0.03 | 1.9 ± 0.04 | 1.9 ± 0.02 |
| Body Mass Index | 25.9 ± 1.9 | 1.92 ± 1.9 | 25.0 ± 1.2 |
| Age at the beginning of disease (average) | 45.0 ± 5.3 | 44.2 ± 5.1 | 43.6 ± 4.9 |
| Duration of disease (average) | 5.2 | 6.7 | 4.8 |
| Was the treatment conducted (yes, no, amount) | yes-1, no -11 | yes-3, no-10 | no-5 |
| Comorbid physic pathological disorders: | | | |
| Anaxiophobic | 41.6% | 46.1% | 40% |
| Mixed anxiety | 33.3% | 30.8% | 40% |
| Anxiety-depressive Adaptation disorder | 25.1% | 23.1% | 20% |

TABLE 2-continued

Characteristics of study patients with erectile dysfunction (n = 30)

| Values | Patients treated by remedy 1 (n - 12) | Patients treated by remedy 2 (n = 13) | Patients of control group (n = 5) |
|---|---|---|---|
| Somatic diseases: | | | |
| CVD | 33.3% | 38.4% | 20.0% |
| Diabetes | 8.3% | 7.6% | — |
| Smoking | 41.6% | 46.5% | 40% |
| Gastrointestinal | 33.3% | 30.7% | 40% |
| Prostate | 41.6% | 30.7% | — |

Patient clinical characteristics (treatment onset with "Remedy 1" and "Remedy 2") did not have significant differences in the experimental and control groups showed.

The average age of the patients was 48.1±6.0 years, average duration of erectile disorder—5.6±2.7 years. Males with higher education (58.5%) were predominated. By family status patients were mostly married men (81.4%). The majority of the patients had weak (20%) and a weakened type of the average sexual constitution (55%).

Assessment of risk factors for smoking was detected in 42.7%, higher body mass index—53.3%; cardiovascular diseases (hypertension, ischemic heart disease in history) were observed in 30.6% of patients.

According to the results of clinical and psychopathological study anxiety-phobic disorder was diagnosed in 42.6%, mixed anxiety-depressive disorder—34.7%, adaptation disorder—22.7% patients. Analysis of test results by Mini-Mult scale showed high levels of hypochondria in 86.7%, depression—54.3%, psychasthenia—52.7% patients. Average scores on hypochondria scale were 62 points, psychasthenia—57 points, depression—53 points and schizoid—51 points.

Sexual dysfunction in all patients included in the study manifested as difficulty in the onset or maintaining erection sufficient for satisfactory sexual intercourse in the absence of evident signs of organic pathology of sexual sphere, corresponding to ICD-10, "the lack of genital response" (F52.2).

Against therapy with "Remedy 1" and "Remedy 2" in the experimental groups on the 7th day of treatment patients reported a subjective improvement in mood, increased self-esteem and confidence in their sexual opportunities, reducing tension and conflicts in family relationship, as well as increased frequency of spontaneous erections.

The study of efficacy of "Remedy 1" and "Remedy 2" on sexual function of patients given clinical and dynamic changes in the level of blood testosterone revealed the following (Table 3):

TABLE 3

Dynamics of testosterone against therapy

| | Average totals | | | | | |
|---|---|---|---|---|---|---|
| | Group 1 (n = 12) | | Group 2 (n = 13) | | Group 3 (n = 5) | |
| Studied parameters | Before treatment | After 28 days of treatment | Before treatment | After 28 days of treatment | Before treatment | After 28 days of treatment |
| Total testosterone | 11.8 ± 4.4 | 14.6 ± 5.2 | 14.5 ± 4.7 | 17.3 ± 5.6 | 12.9 ± 4.7 | 13.1 ± 5.8 |

In group 1 with "Remedy 1" administration testosterone levels increased by 23.7%, in the 2 group with "Remedy 2"—by 19.8%.

The growth of sexual activity indicators—libido and erection—with the treatment of "Remedy 1" and "Remedy 2" by the Day 28 of treatment was detected in 66.7 and 61.5% patients, respectively, average increase of libido was 28.0 and 24.3%, erection—21.4 and 17.8%, respectively. Dynamic changes of sexual activity indicators (libido and erection) and psycho-emotional state of patients with erectile dysfunction and comorbid anxiety and depressive disorders are presented in Table 4.

TABLE 4

Results of therapy and tests performed on day 28 of treatment

| | Average totals (in points) | | | | | |
|---|---|---|---|---|---|---|
| | Group 1 | | Group 2 | | Group 3 | |
| Investigated parameters | Before treatment | On day 28 of treatment | Before treatment | On day 28 of treatment | Before treatment | On day 28 of treatment |
| SFM questionnaire Sexual function status questionnaire | 18.8 ± 3.2 | 21.9 ± 3.5* | 18.4 ± 3.1 | 21.4 ± 3.2* | 18.9 ± 2.1 | 19.1 ± 2.5 |
| Libido | 2.8 | 3.6 | 2.7 | 3.4 | 2.9 | 3.0 |
| Erection | 3.0 | 3.6 | 2.9 | 3.4 | 3.0 | 3.0 |

TABLE 4-continued

Results of therapy and tests performed on day 28 of treatment

| | Average totals (in points) | | | | | |
|---|---|---|---|---|---|---|
| | Group 1 | | Group 2 | | Group 3 | |
| Investigated parameters | Before treatment | On day 28 of treatment | Before treatment | On day 28 of treatment | Before treatment | On day 28 of treatment |
| HADSscale | | | | | | |
| Anxiety | 11.2 ± 0.8 | 6.9 ± 0.5** | 10.9 ± 1.0 | 7.1 ± 0.5** | 11.4 ± 0.3 | 8.5 ± 0.5 |
| Depression | 9.1 ± 0.4 | 6.2 ± 0.3* | 9.5 ± 0.7 | 6.1 ± 0.3* | 10.0 ± 0.4 | 7.9 ± 0.8 |
| Clinical effect Abs. | | 8 | | 8 | | 1 |
| Clinical effect % | | 66.7 | | 61.5 | | 20.0 |

Note:
*p < 0.05,
**p < 0.001

The therapeutic effect of the drugs was more pronounced in relatively young men in the absence of the above mentioned risk factors and expressed anxiety-depressive psychopathology disorders. It is shown by evidence of the effectiveness of the drug in the treatment of erectile dysfunction in 75.2% of cases in men under 40 years old.

In the course of therapy with "Remedy 2" (from 2 to 4 days of treatment) 2 patients had transient diarrhea. It resolved spontaneously. Tolerability of "Remedy 1" and "Remedy 2" is good.

Against treatment with "Remedy 1" and "Remedy 2" erectile dysfunction is common in hospital anxiety and depression, and requires adequate specific therapy.

The claimed remedy is a combination of biologically active drug that is based on L-arginine, icariin (Rhaponticum carthamoides extract), Male bee brood, pollen (bee pollen), zinc citrate, vitamin B6, it has the ability to increase sexual desire and improve the quality of erections and, therefore, is a vegetable alternative to the treatment of sexual disorders in male.

Use of "Remedy 1" showed an increase in the level of testosterone in the blood serum in 23.7%, "Remedy 1"—19.8% by the Day 28 of treatment.

Indicators of sexual activity—libido and erection—and psycho-emotional state against "Remedy 1" and "Remedy 2" treatment by the Day 28 of treatment were detected in 66.7 and 61.5% patients, respectively. In the group of patients with "Remedy 1" average increase of libido and erection was observed in 28.0 and 21.4%, and in group 2-24.3 and 17.8% patients, respectively. There was significant improvement of mental and emotional state with 50% reduction in the level of anxiety and depression in both the first and second group of patients.

The second study was carried out with all 8 components. Composition of "Remedy 3" in a daily dose was the following:

| Components | Mg of active substance |
|---|---|
| True or false *ginseng* root in terms of saponins | 9 |
| *Leuzea* root in terms of ecdysteroids | 0.15 |
| L-Arginine | 900 |
| Horny goat weed in terms of icariin | 60 |
| Male bee brood in terms of decenoic acid | 0.6 |
| Pollen or beebread in terms of rutin | 48 |
| Zinc citrate in terms of zinc | 9 |
| Vitamin B6 | 1.8 |

Study Objective:
evaluation of the efficacy of "Remedy 3" in the treatment of male sexual dysfunction.

The study investigated clinical features of sexual dysfunctions in studied patients. Effectiveness of "Remedy 3" on the dynamics of testosterone, prolactin and dehydroepiandrosterone sulfate (DHEAS) levels was evaluated by the changes of the values of sexual function (libido and erection) and psycho-emotional state of studied patients.

The study involved 10 men with sexual dysfunction (erectile dysfunction and decreased libido). Inclusion criteria were:

19-60 years old (age limit was associated with frequent detection in men older than 60 years of the severe cerebral organic and physical illnesses and involution processes);

matching of patient's condition at the time of inclusion to diagnostic criteria of ICD 10 for F52—sexual dysfunction (absence or loss of the sexual desire (F 52.0), absence of genital response (F52.2)), accompanied by one of the following neurotic disorders: anxiety-phobic (F40); mixed anxiety-depressive disorder (F41.2) and adaptation disorder (F 43.2);

absence of leading organic lesion in pathogenesis of sexual disorder.

The study did not include patients with alcoholism; drug addiction; anatomical deformity of the penis; proven endocrine causes of ED; decompensated somatic diseases; use other treatment agents for ED and drugs that can cause ED.

The study was conducted by the open method, without placebo control.

During clinical and sexual examination severity and dynamics of sexual pathological symptoms during therapy were evaluated by clinical questionnaire "Sexual Formula for Men" (SFM), IIEF-5 questionnaire (International Index of Erectile Function), scale of assessment of sexual function (Vakina T. N. 2001) (see. appendices 1, 2, 3).

Laboratory and instrumental examinations included complete blood count, urinalysis, quantitative content determination of hormones in blood serum—total testosterone, prolactin and DHEAS—by enzyme-linked immunosorbent assay, as well as transrectal prostate ultrasound. Consultative examination by urologist was performed.

The mental state of the patients was determined by clinical and psychopathological method. Examination of personality characteristics was performed by Mini-Mult questionnaire. Intensity and dynamics of anxiety-depressive disorder symptoms during therapy were evaluated by Hospital Anxiety and Depression Scale (HADS).

The research was conducted as follows (table 5): a preliminary study—1 week (check the inclusion and exclusion criteria, consent to participate in study, medical history, assessment of the general condition of organs and systems, laboratory tests, clinical sexual and psychological testing). Phase of treatment—4 weeks—use of "Remedy 3" at a dose of 2 tablets 3 times a day 30 minutes before meals with the registration of changes in the general condition of the patient and side effects. Final evaluation of the treatment was carried out in 28-30 days with the assessment by SFM questionnaire, scale of assessment of sexual function, hormonal tests, HADS scale, identification of drug tolerability.

TABLE 5

Scheme of patients examination

| Documents and research methods | Stage I (enrollment in the study) Screening and randomization (days 0-7) | Stage II (Treatment by Remedy 3) Days of treatment | | | | |
|---|---|---|---|---|---|---|
| | | 3 | 7 | 14 | 21 | 28 |
| Informed consent for participation in the study | V | — | — | — | — | — |
| CRF | V | V | V | V | V | V |
| SFM questionnaire | V | — | — | — | — | V |
| IIEF-5 questionnaire | V | — | — | — | — | — |
| State of sexual function questionnaire (Vakina T.N. 2001) | V | — | — | — | — | V |
| Level of total serum testosterone, prolactin, DHEAS | V | — | — | — | — | V |
| HADS scale | V | — | — | — | — | V |
| Mini-Mult questionnaire | V | — | — | — | — | — |
| TRUS of prostate | V | — | — | — | — | — |
| Consultation of urologist | V | — | — | — | — | — |
| Blood and urine tests | V | — | — | — | — | V |
| Evaluation of side effects | — | V | V | V | V | V |

Effectiveness evaluation was based on the dynamics of indicators of the scale of assessment of sexual function, "Sexual Formula for Men" (SFM) questionnaire, HADS scale, the results of hormone tests, evaluation of the clinical effectiveness of physician therapy.

During assessment of clinical efficacy by the patient end result was defined as excellent (no complaints, resumption of sexual activity in full extent), good (considerable improvement, but still with some complaints), satisfactory (the patient noted improvement, but full recovery of sexual activity was absent), without effect.

The results were processed using the "STATISCTICA-6.0" statistical program.

According to the results of the study all 10 patients completed the study. General characteristics of the patients included in the study are presented in the Table 6.

TABLE 6

Characteristics of the studied patients with sexual dysfunction (n = 10)

| Indicators | Patients treated by EROMAX 3 (n = 10) |
|---|---|
| Age (average value) | 46.9 ± 5.1 |
| Family status | |
| Single | 10% |
| Married | 60% |
| Divorced | 30% |
| Civil marriage | — |

TABLE 6-continued

Characteristics of the studied patients with sexual dysfunction (n = 10)

| Indicators | Patients treated by EROMAX 3 (n = 10) |
|---|---|
| Level of education | |
| Higher | 80% |
| Secondary professional | 20% |
| Secondary | — |
| Anthropometric parameters | 1.89 ± 0.04 |
| Trochanteric index | 26.9 ± 2.9 |
| Body Mass Index | 41.6 ± 6.0 |
| Age at the beginning of disease (average) | 4.9 ± 2.3 |
| Was the treatment conducted (yes, no, amount) | yes - 4, no - 6 |
| Comorbid physic pathological disorders: | |
| Anxiofobic | 10% |
| Mixed anxiety-depressive | 30% |
| Adaptation disorders | 60% |
| Somatic diseases: | |
| CVD | 70% |
| Diabetes | 10% |
| Smoking | 30% |
| Gastrointestinal diseases | 30% |
| Prostate disease | 40% |

Average age of patients was 46.9±5.1 years, average duration of sexual disorders—4.9±2.3 years. Men with higher education dominated (80%). By family status patients were mostly married men (60%). The majority of the patients had weak (50%) and a weakened type of the average sexual constitution (30%).

Assessment of risk factors for smoking was detected in 30%, increased body mass index—50%; cardiovascular diseases (hypertension, ischemic heart disease in history) were observed in 70% of patients.

Most of the patients had a history of significant mental and physical stress, and the clinical and psychopathological study revealed adaptation disorders in 60% patients. Analysis of test results on Mini-Mult scale showed high levels of hypochondria in 60%, depression—50%, psychasthenia—50% patients. Average scores on psychasthenia scale were 62.8 points, hypochondria—59.8 points, depression—52 points and hysteria—51 points.

Sexual dysfunction in all patients included in the study manifested as decreased libido with a decrease of sexual fantasies, sexual incentives search, thoughts about the sexual side of life and the difficulties in the attack or sustain an erection sufficient for satisfactory sexual intercourse, with the absence of evident signs of organic pathology of the sexual sphere, accompanied by anxiety and depressive symptoms.

The main complaints of patients reflecting the clinic of androgen according to age groups are presented in Table 7.

TABLE 7

The main complaints of patients that are typical for clinical androgen deficiency

| Symptoms | Age groups | |
|---|---|---|
| | Under 45 years (n = 2) | Above 45 years (n = 8) |
| Genitourinary disorders | | |
| decrease of libido | 50% | 100% |
| erectile dysfunction | 100% | 75% |
| reduction of orgasm brightness | 50% | 75% |
| Vegeto-vascular disorders | | |
| Sudden redness of face, neck | — | 37.5% |
| Blood pressure fluctuations | — | 75% |
| Cardialgia | — | 50% |
| Dizziness | — | 25% |
| Lack of air | — | 37.5% |
| Excessive sweating | | 50% |
| Psychoemotional disorders | | |
| Increased irritability | 100% | 75% |
| Reduction of the ability to concentrate attention | — | 75% |
| Reduction of cognitive function, memory | | |
| Depression | 50% | 50% |
| Insomnia | 50 | 50% |
| Reduction of "vital energy" | — | 25% |
| | | 75% |
| Somatic disorders | | |
| Decrease of muscle mass and strength | — | 37.5% |
| Increase of adipose tissue amount | — | 75% |
| Osteoporosis | — | 12.5% |
| Decreased tone and skin thickness ("flabby" skin) | — | 25% |

It is noteworthy that in the age group under 45 years decreased libido was observed in all patients (100%), with erectile dysfunction in 75% of cases (Table. 7).

The analysis of erectile dysfunction according to the IIEF-5 scale showed that 1 patient (10%, 22 points) had a value within the normal range; mild erectile dysfunction was detected in 5 cases (50%, 18 points average), moderate ED—in 4 (40%, 14 points average).

Against the therapy by "Remedy 3," the majority of patients (60%) by the Day 5-7 had subjective improvement mood, increased self-esteem and confidence in their sexual opportunities, reducing tension and reducing conflict in the family relationship, as well as increased frequency of nocturnal erections.

The study of the efficacy of "Remedy 3" on sexual function of patients taken into account clinical and dynamic changes in the level of testosterone, prolactin and dehydroepiandrosterone sulfate (DHEAS) in serum showed the following (Table 8):

TABLE 8

Dynamics of testosterone, prolactin and DHEAS in serum against the therapy

| Investigated parameters | Before treatment | After 28 days of treatment | Normal values | P |
|---|---|---|---|---|
| Total Testosterone* | 11.8 ± 4.4 | 17.1 ± 5.7 | 12.1-38.3 nmol/L | <0.02 |
| Prolactin * | 548 ± 136 | 285 ± 60 | 24.5-467 mU/L | <0.02 |
| DHEAS | 1.2 ± 0.3 | 1.4 ± 0.7 | 1.0-4.2 mg/ml | >0.054 |

Against use of "Remedy 3" there were significantly elevated levels of total testosterone (p<0.02) and DHEAS against the lowered prolactin levels (p<0.02) (the latter could also be regarded as anti-stress improving trends in the studied group of patients).

Rate of growth of testosterone levels against use of "Remedy 3" was 44.9%. These changes of hormonal status helped to reduce the number of patients' complaints on vegetosovascular disorders—sudden flushing of the face, neck, increased sweating, feeling of short of breath, fluctuations of blood pressure, as well as on psycho-emotional sphere. Patients reported mood stabilization, addition of "vital energy force", improvement of concentration, memory, normalization of sleep. The amount of adipose tissue decreased which revealed itself in a decrease of waist circumference by an average of 3.9 cm for 1 month.

At the time of the control evaluation—after 4 weeks of treatment—patients had significant change in scale of sexual function assessment: libido—4.0 points versus baseline of 2.8 (p<0.02), average increase of the libido was 42.8%, erection—3.8 points versus baseline of 2.9 (p<0.032), average increase of the erection was 31%.

Assessment of sexual function in accordance with the SFM questionnaire before treatment revealed general decline of male copulation cycle values. Against therapy with "Remedy 3" total score of male sexual function increased from 17.7±2.5 to 23.8±2.9 (p<0.02). Among the structural indicators of SFM mental component of the male copulation cycle improved more significantly that resulted in increase of libido and overall satisfaction with sexual intercourse in the studied patients.

Dynamic changes of comorbid psychoemotional disorders parameter—anxiety and depression—of patients with sexual dysfunction are shown in Figure 3. If before treatment the average level of anxiety was regarded as a clinical one and was 11.5±0.6 points on HADS, after treatment it decreased to normal level—6.9±0.3 points (p<0.02). The average level of depression on HADS scale at the beginning of treatment was approaching to clinical one—10.8±0.5 points; at control day 28 the depression values were reduced to normal levels—6.7±0.3 (p<0.02).

During therapy with "Remedy 3" (from Day 2 to Day 4 of treatment) 3 patients had transient diarrhea. It resolved spontaneously. Indicators of blood count, urinalysis, and biochemical blood tests were within the normal range before the start of treatment and at its end. Overall tolerability of "Remedy 3" was good.

In evaluating the clinical efficacy of the treatment 2 (20%) patients evaluated results as "excellent"—the absence of complaints, the resumption of sexual life in full extent, 6 (60%) patients—as "good"—a considerable improvement but still with some complaints, and 2 (20%)—as "satisfactory"—improvement, but full recovery of sexual activity was absent, but the latter ones had marked improvement in the parameters of hormonal status with higher levels of total testosterone and decrease of prolactin.

Thus, sexual dysfunction is common in patients with anxiety and depression and requires an adequate specific therapy. "Remedy 3" is a combined biologically active drug that is based on L-arginine, ginseng root, Leuzea root, horny goat weed extract, pollen (bee brood), zinc citrate, vitamin B6, and it is able to increase sexual desire and improve the quality of erection, and hence is a natural and safe alternative effective treatment for sexual dysfunction in males. Use of "Remedy 3" showed a significant increase of testosterone level (average increase of 44.9%) against prolactin level decrease as well as a tendency to DHEAS increase by day 28 of treatment. Parameters of sexual activity—libido and erection—against use of "Remedy 3" significantly changed: the average increase of libido was 42.8%, erection—31%. The therapy with "Remedy 3" led to stabilization of vegetative vascular system, as well as significant improvement of mental and emotional state of patients with reduction of anxiety and depressive disorders.

Appendices:

Appendix 1 - Questionnaire

Appendix 2 - IIEF-5 Questionnaire (International Index of Erectile Function, version with 5 questions)

Appendix 3 – Scale of evaluation of sexual function

Appendix 4 - Quantification of hormones in blood serum

Appendix 5 - Hospital Anxiety and Depression Scale (HADS)

APPENDIX 1

Sexual Formula for Men (SFM)

Special questionnaire used in the sexual practice for preliminary assessment of the sexual sphere in males. The questionnaire consists of 10 sections (marked by Roman numerals) in each section patient's responses are indicated by numbers from 0 to 4. A patient before the test is invited to complete a questionnaire, marking in each section a statement that most closely matches his condition at the time of doctor's appointment.

I. The need for sexual relations

How often does the strong desire to perform sexual intercourse (regardless of the penis tension) occur:

0 - Never or no more than once a year.

1 - Several times a year, but not more often than once a month.

2 – From two to four times a month.

3 - Twice or more often in a week.

4 - Every day once or more times,

II. Mood before sexual intercourse

0 - Strong fear of failure and, therefore, attempts have never been made.

1 - Expressed uncertainty, and, therefore, I'm looking for an excuse to evade attempts.

2 - Some uncertainty, but I do not evade attempt (or – I made copulation to satisfy wife, without inner motivation, or – I perform intercourse to test myself)

3 - Primarily - a desire for enjoyment and having a woman; I make intercourse without fear.

4 - Always just a thirst for pleasure with a woman, never feel the slightest doubts.

III. Sexual proactivity

I perform act aimed at the immediate implementation of sexual intercourse

0 - I do not perform such acts or perform them with intervals of not less than one year.

1 - Several times a year, but not more than once per month.

2 - Several times per month, but not more often than once a week.

3 - Twice or more often in a week.

4 - Every day, once or several times.

IV. Frequency of sexual intercourse

I manage to perform intercourse (though not quite in full form, that is, short-term or partial tension of penis)

0 – I have never been able.

1 - Very rare.

2 - In most cases.

3 - In normal situations, always.

4 - In any situation and always, even if the circumstances are not favorable.

V. Tension of penis (erection)

0 - Erection does not occur under any circumstances.

1 - without sexual intercourse erection is sufficient, but at the time of sexual intercourse it weakens, penis penetration is not possible.

2 – I have to use force or local manipulation to cause an erection sufficient for penetration (or erection weakens after penetration but before ejaculation).

3 – Erection is incomplete but the penetration is possible effortlessly.

4 - Erection occurs in all conditions, even the most unfavorable.

VI. The duration of sexual intercourse

Ejaculation occurs:

0. - does not occur under any circumstances.

0.5 - occurs at every intercourse, intercourse is prolonged; sometimes it has exhausting character.

1 - before the penis penetration or at the time of penetration.

2 – in a few seconds after penetration.

2.5 - approximately within 15-20 movements.

3-4 – in 1-2 minutes or longer (indicate the approximate duration).

VII. The frequency of sexual emission

Ejaculation occurs with intercourse (or nocturnal emissions, masturbation, etc.) on average 0. - does not occur or occurs no more than once a year.

1 - several times a year, but not often than once a month.

2 - several times a month, but not often than once a week.

3 - twice or more often in a week.

4 - every day, one or more times.

VIII. The mood after sexual intercourse (or failed attempt)

0. - Extreme depression, a feeling if disaster (or aversion to his wife).

1 -Disappointment.

2 - Indifference (or some sediment from the understandings that a woman feels dissatisfied).

3 - Satisfaction and pleasant fatigue.

4 - Complete satisfaction and elation.

IX. Measuring the success of sexual life

0. - Women do not want to have sex with me

1 - Women express criticisms.

2 - Sexual life is going on with varying degrees of success.

3 - Sexual life is generally successful.

4 – I am able to satisfy a woman under all circumstances.

APPENDIX 2 - IIEF-5 questionnaire (International Index of Erectile Function, variant with 5 questions)

| How do you evaluate your confidence in that you can achieve and maintain an erection? | | Very low 1 | Low 2 | Medium 3 | High 4 | Very high 5 |
|---|---|---|---|---|---|---|
| In case of erection due to sexual stimulation how often do you have an erection strong | Sexual activity is absent 0 | Almost never or never 1 | Several times (far less than half of | Someti mes (about a half of cases) | In most cases (more than a half of | Almost always or always 5 |

| | | | | | cases) 2 | 3 | cases) 4 | |
|---|---|---|---|---|---|---|---|---|
| enough for penis penetration into the vagina? | | | | | | | | |
| In case of sexual intercourse how often do you manage to maintain an erection after penis penetration into the vagina? | There were no attempt for sexual intercourse 0 | Almost never or never 1 | Several times (far less than half a cases) 2 | Sometimes (about a half of cases) 3 | In the most cases (more than a half a cases) 4 | Almost always or always 5 |
| In case of sexual intercourse to what extent do you find it difficult to maintain an erection to complete intercourse? | There were no attempt for sexual intercourse 0 | Extremely difficult 1 | Very difficult 2 | Difficult 3 | Quite difficult 4 | Not difficult 5 |
| In case of sexual intercourse attempts how often you were satisfied? | There were no attempt for sexual intercourse 0 | Almost never or never 1 | Several times (far less than half of cases) 2 | Sometimes (about a half of cases) 3 | In the most cases (more than a half of cases) 4 | Almost always or always 5 |

All questions are relating to the state within the last 6 months.

Total score _____

APPENDIX 3 - Scale of evaluation of sexual function (Vakina T.N., 2001)

| Erection | | | Libido | | |
|---|---|---|---|---|---|
| *Symptoms* | *Before treatment* | *After* | *Symptoms* | *Before treatment* | *After* |
| Complete absence | 1 | 1 | Complete absence of libido | 1 | 1 |
| Erection atony with the impossibility of spontaneous penetration | 2 | 2 | Marked decrease of libido (rare intercourses with the steady rhythm of sexual life completely broken) | 2 | 2 |
| Erection atony with the possibility of spontaneous penetration breaking the steady rhythm of a sexual life | 3 | 3 | Moderate decrease of libido (steady rhythm of sexual life is changed, but sexual activity is maintained) | 3 | 3 |
| Erection atony not affecting the steady rhythm of a sexual life | 4 | 4 | Slight decrease of libido (does not break the rhythm of sexual life) | 4 | 4 |
| Normal adequate erection | 5 | 5 | Normal libido | 5 | 5 |
| Total | | | | | |

Test method: enzyme-linked immunosorbent test

| No | Hormones | Reference ranges | Units of measurement |
|---|---|---|---|
| 1 | Total testosterone | mIU/L | 12.1-38.3 |
| 2 | DHEAS | nmol/L | 1.0-4.2 |
| 3 | Prolactin | µg/ml | 24.5 - 467 |

In several studies it was shown that a decrease of testosterone concentration results in increased deposition of fat cells in the corpora cavernous which causes a degeneration of the smooth muscle cells which results in poor elasticity of cavernous tissue with formation of venous cavernous erectile insufficiency.

Kalinichenko S.Y. summarized data on the effect of androgen deficiency on erectile function:

- Reduction of relaxation of smooth muscle cells of the cavernous tissue;
- Decrease of nitric oxide production;
- Increased apoptosis of smooth muscle cells;
- Increased number of fat cells.

*However, testosterone deficiency does not always affect the mechanism of erection, but it is a pathogenic factor in libido reduction.* Numerous studies of the effects of testosterone on the individual components of the copulative cycle showed that the most significant positive correlation was found between its concentration in blood and sexual desire (Jordan W. et al. 1998, Clopper, 1993). It is assumed that androgens increase desire by increasing the sensitivity of certain centers in the limbic system and hypothalamus, as well as by increasing overall activity and vitality of the body due to the stimulating effect of androgens on metabolism. This is confirmed by the fact that testosterone preparations are the most effective drugs to increase libido and stimulate the orgasmic experiences intensity.

A lack of androgens leads to a decrease of sexual interest and activity. Effect on erectile function is more complicated (Kwan et al., 1983). Therefore, an erection could be observed over the years (Heim, 1981) after castration. Similarly, the gradual recovery of male sexual behavior in case of chronic androgen deficiency does not immediately occur under the influence of testosterone replacement therapy.

Prolactin is a hormone involved in the growth of the prostate. Prolactin (PRL) is necessary to maintain maximal steroidogenic activity of Leydig cells in the presence of luteinizing hormone (LH); it increases the number of receptors for LH.

Under physiological conditions, stimulation of PRL release occurs during sleep, stress, physical activity, receiving protein foods, hypoglycemia. PRL is often called a stress hormone, although the effect of mental and psychological stress on its release is not clearly demonstrated. Pathological hyperprolactinemia may be a manifestation of independent hypothalamic pituitary disease or as well a syndrome in the structure of various endocrinopathies, somatogenic and neuropsychiatric disorders (acromegaly, primary hypothyroidism, chronic renal failure, chronic prostatitis, hepatic cirrhosis).

For men, symptoms of hyperprolactinemia include reduced or absent libido and potency, reduction of secondary sexual features, infertility due to oligospermia and gynecomastia.

Chronic hyperprolactinemia in males is associated with inhibited secretion of gonadotropin-releasing hormone (GnRH), and hence of gonadotropic secretion, resulting in reduced total testosterone in serum.

It is supposed that direct depletion of dopamine (DA) in dopaminergic neurons may play a major role in the male copulation behavior, especially in reducing libido, concomitant with hyperprolactinemia.

DHEAS (dehydroepiandrosterone sulfate) is a secondary source of testosterone in men, produced primarily by the adrenal glands. DHEAS has relatively weak androgenic activity which for non-sulfonated hormone is about 10% of the testosterone level. However, its biological activity is enhanced by the relatively high concentration of serum - a hundred times superior to testosterone - as well as due to the weak affinity for steroid-binding ß- globulin. This hormone is a precursor of both estrogen and testosterone.

DHEAS (and DHEA) are present in the tissues of the brain and are regarded as a neurosteroid involved in the regulation of behavior and psychophysiological reactions (stress reactions, intelligence, memory, attention, sleep). Decrease of circulating levels of DHEA and, accordingly, the ratio of DHEA / cortisol is associated with the CNS disorders such as depression, memory disorders, chronic fatigue syndrome, decreased libido, Alzheimer's disease.

By the age of 50, DHEA levels are reduced by 30% compared with those of men of the age of 30. It is widely believed that the decrease of DHEAS occurs in parallel with the decrease of well-being, and that exogenous DHEA substitution leads to an improvement in quality of life parameters.

APPENDIX 5 - HOSPITAL ANXIETY AND DEPRESSION SCALE (HADS)

In clinical practice HADS scale is used to identify and assess the severity of anxiety – depressive disorders in screening studies, as well as to assess the effectiveness of psycho corrective therapy. Scale is filled in by the patient alone within 15-20 min.
HADS contains 14 symptoms and consists of two subscales - anxiety (A), and depression (D). Anxiety assessment includes odd items; depression – even ones. Each parameter corresponds to four choices, reflecting its presence and severity.

| | |
|---|---|
| A<br>I feel tension, I feel strange<br>☐ 3 all the time<br>☐ 2 often<br>☐ 1 from time to time, sometimes<br>☐ 0 not at all | D<br>I think I've started doing everything very slowly<br>☐ 3 almost all the time<br>☐ 2 often<br>☐ 1 sometimes<br>☐ 0 not at all |
| D<br>What used to bring me great pleasure now causes the same feeling<br>☐ 0 definitely it is so<br>☐ 1 probably it is so<br>☐ 2 in small extent it is so<br>☐ 3 not at all | A<br>I feel internal tension or shivering<br>☐ 0 do not feel it at all<br>☐ 1 sometimes<br>☐ 2 often<br>☐ 3 vey often |
| A<br>I feel fear, it seems as if something terrible may be about to happen<br>☐ 3 definitely it is so, and fear is very strong<br>☐ 2 yes, it is so, but fear is not very strong<br>☐ 1 sometimes, but it does not bother me<br>☐ 0 do not feel it at all | D<br>I do not take care after my appearance<br>☐ 3 definitely it is so<br>☐ 2 I do not give it as much time as it is required<br>☐ 1 May be I've begun to pay less attention to this<br>☐ 0 I take care of myself in the same way as before |
| D<br>I'm able to laugh and see something funny in a particular event<br>☐ 0 definitely it is so<br>☐ 1 maybe it is so<br>☐ 2 it is so only in small extent<br>☐ 3 not able at all | A<br>I feel restless like I always need to move<br>☐ 3 definitely it is so<br>☐ 2 maybe it is so<br>☐ 1 it is so in some extent<br>☐ 0 do not feel like this at all |

| A<br>Restless thoughts are spinning in my head<br>☐ 3 constantly<br>☐ 2 most of the time<br>☐ 1 from time to time and not so often<br>☐ 0 only sometimes | D<br>I believe that my business (employment, hobbies) can bring me a sense of satisfaction<br>☐ 0 in the same way as usually<br>☐ 1 yes, but not to the same extent as before<br>☐ 2 much less than usually<br>☐ 3 do not think so |
|---|---|
| D<br>I feel vivacious<br>☐ 3 do not feel like this at all<br>☐ 2 very rarely<br>☐ 1 sometimes<br>☐ 0 almost all the time | A<br>I have had a sudden feeling of panic<br>☐ 3 very often<br>☐ 2 quite often<br>☐ 1 not so often<br>☐ 0 not at all |
| A<br>I can easily sit down and relax<br>☐ 0 definitely it is so<br>☐ 1 maybe it is so<br>☐ 2 only sometimes it is so<br>☐ 3 can't do it at all | D<br>I can get pleasure from a good book, radio or TV program<br>☐ 0 often<br>☐ 1 sometimes<br>☐ 2 rarely<br>☐ 3 very rarely |

Qualifications of subscales of anxiety and depression are performed separately for the following conclusions: 0 to 7 points - no significant signs of anxiety and depression; from 8 to 10 points - subclinical anxiety/depression; 11 and above points - clinically expressed anxiety/depression.

in males. The questionnaire consists of 10 sections (marked by Roman numerals) in each section patient's responses are indicated by numbers from 0 to 4. A patient before the test is invited to complete a questionnaire, marking in each section a statement that most closely matches his condition at the time of doctor's appointment.

I. The Need for Sexual Relations
How often does the strong desire to perform sexual intercourse (regardless of the penis tension) occur:
0—Never or no more than once a year.
1—Several times a year, but not more often than once a month.
2—From two to four times a month.
3—Twice or more often in a week.
4—Every day once or more times, II. Mood Before Sexual Intercourse
0—Strong fear of failure and, therefore, attempts have never been made.
1—Expressed uncertainty, and, therefore, I'm looking for an excuse to evade attempts.
2—Some uncertainty, but I do not evade attempt (or—I made copulation to satisfy wife, without inner motivation, or—I perform intercourse to test myself)
3—Primarily—a desire for enjoyment and having a woman; I make intercourse without fear.
4—Always just a thirst for pleasure with a woman, never feel the slightest doubts.

III. Sexual Proactivity
I perform act aimed at the immediate implementation of sexual intercourse
0—I do not perform such acts or perform them with intervals of not less than one year.
1—Several times a year, but not more than once per month.
2—Several times per month, but not more often than once a week.
3—Twice or more often in a week.
4—Every day, once or several times.

IV. Frequency of Sexual Intercourse
I manage to perform intercourse (though not quite in full form, that is, short-term or partial tension of penis)
0—I have never been able.
1—Very rare.
2—In most cases.
3—In normal situations, always.
4—In any situation and always, even if the circumstances are not favorable.

V. Tension of Penis (Erection)
0—Erection does not occur under any circumstances.
1—without sexual intercourse erection is sufficient, but at the time of sexual intercourse it weakens, penis penetration is not possible.
2—I have to use force or local manipulation to cause an erection sufficient for penetration (or erection weakens after penetration but before ejaculation).
3—Erection is incomplete but the penetration is possible effortlessly.
4—Erection occurs in all conditions, even the most unfavorable.

VI. The Duration of Sexual Intercourse
Ejaculation occurs:
0—does not occur under any circumstances.
0.5—occurs at every intercourse, intercourse is prolonged; sometimes it has exhausting character.
1—before the penis penetration or at the time of penetration.
2—in a few seconds after penetration.
2.5—approximately within 15-20 movements.
3-4—in 1-2 minutes or longer (indicate the approximate duration).

VII. The Frequency of Sexual Emission
Ejaculation occurs with intercourse (or nocturnal emissions, masturbation, etc.) on average
0—does not occur or occurs no more than once a year.
1—several times a year, but not often than once a month.
2—several times a month, but not often than once a week.
3—twice or more often in a week.
4—every day, one or more times.

VIII. The Mood After Sexual Intercourse (or Failed Attempt)
0—Extreme depression, a feeling if disaster (or aversion to his wife).
1—Disappointment.
2—Indifference (or some sediment from the understandings that a woman feels dissatisfied).
3—Satisfaction and pleasant fatigue.
4—Complete satisfaction and elation.

IX. Measuring the Success of Sexual Life
0—Women do not want to have sex with me
1—Women express criticisms.
2—Sexual life is going on with varying degrees of success.
3—Sexual life is generally successful.
4—I am able to satisfy a woman under all circumstances.

X. Duration of Sexual Disorders
0—From the beginning of sexual activity.
1—Longer than half a year.
2—Less than half a year.
3—Currently there are no problems but they occurred in the past (particularly at the beginning of sexual activity).
4—I do not know what is it having difficulties in sexual life.

The numbers 0, 1, 2 in each of the ten parameters reflect different degrees of decreased sexual function, 3—above average rate for middle-aged men, 4—strong sexual constitution or a period of youthful hypersexuality.

Structural indicators reflect: I—the state of preliminary readiness associated with neuroendocrine libido assurance; II, III—the state of psychic sphere, which is expressed in the mood before coitus, sexual activity. Indicators IV, V reflect the implementation of the objective parameters of sexual activity: the frequency of coitus, the quality of erections. Indicators VII and VI objectively characterize the ejaculatory function. Indicators VIII and IX represent a subjective assessment of sexual intercourse by the man and his partner. The SFM analysis takes into account each of received responses, and then their numerical expressions are summarized. Thus for a statistically average norm SFM is 30. For the patients with sexual disorders and false sexual disorders SFM values differ from the average downwards.

APPENDIX 2

IIEF-5 questionnaire (International Index of Erectile Function, variant with 5 questions)

| | Very low | Low | Medium | High | Very high |
|---|---|---|---|---|---|
| How do you evaluate your confidence in that you can achieve and maintain an erection? | 1 | 2 | 3 | 4 | 5 |

APPENDIX 2-continued

IIEF-5 questionnaire (International Index of Erectile Function, variant with 5 questions)

| | | | | | | |
|---|---|---|---|---|---|---|
| In case of erection due to sexual stimulation how often do you have an erection strong enough for penis penetration into the vagina? | Sexual activity is absent 0 | Almost never or never 1 | Several times (far less than half of cases) 2 | Sometimes (about a half of cases) 3 | In most cases (more than a half of cases) 4 | Almost always or always 5 |
| In case of sexual intercourse how often do you manage to maintain an erection after penis penetration into the vagina? | There were no attempt for sexual intercourse 0 | Almost never or never 1 | Several times (far less than half a cases) 2 | Sometimes (about a half of cases) 3 | In the most cases (more than a half a cases) 4 | Almost always or always 5 |
| In case of sexual intercourse to what extent do you find it difficult to maintain an erection to complete intercourse? | There were no attempt for sexual intercourse 0 | Extremely difficult 1 | Very difficult 2 | Difficult 3 | Quite difficult 4 | Not difficult 5 |
| In case of sexual intercourse attempts how often you were satisfied? | There were no attempt for sexual intercourse 0 | Almost never or never 1 | Several times (far less than half of cases) 2 | Sometimes (about a half of cases) 3 | In the most cases (more than a half of cases) 4 | Almost always or always 5 |

All questions are relating to the state within the last 6 months.
Total score _____

Norm—no ED—21-25 points, mild ED—16-20 points, moderate ED—11-15 points and significant ED—5-10 points.

APPENDIX 3

Scale of evaluation of sexual function (Vakina T. N., 2001)

| | Erection | | | Libido | |
|---|---|---|---|---|---|
| Symptoms | Before treatment | After | Symptoms | Before treatment | After |
| Complete absence | 1 | 1 | Complete absence of libido | 1 | 1 |
| Erection atony with the impossibility of spontaneous penetration | 2 | 2 | Marked decrease of libido (rare intercourses with the steady rhythm of sexual life completely broken) | 2 | 2 |
| Erection atony with the possibility of spontaneous penetration breaking the steady rhythm of a sexual life | 3 | 3 | Moderate decrease of libido (steady rhythm of sexual life is changed, but sexual activity is maintained) | 3 | 3 |
| Erection atony not affecting the steady rhythm of a sexual life | 4 | 4 | Slight decrease of libido (does not break the rhythm of sexual life) | 4 | 4 |
| Normal adequate erection | 5 | 5 | Normal libido | 5 | 5 |
| Total | | | | | |

Questionnaire includes 10 questions designated by the numbers. Each question has 6 possible answers that have a rating from 1 to 5. One corresponds to an extreme degree of dysfunction, five—the maximum of the function intensity, which is typical for individuals with a strong type of sexual constitution.

APPENDIX 4

QUANTIFICATION OF HORMONES IN BLOOD SERUM
Test method: enzyme-linked immunosorbent test

| No | Hormones | Reference ranges | Units of measurement |
|---|---|---|---|
| 1 | Total testosterone | mIU/L | 12.1-38.3 |
| 2 | DHEAS | nmol/L | 1.0-4.2 |
| 3 | Prolactin | µg/ml | 24.5-467 |

Testosterone is the main male sex hormone, mainly synthesized in the testes by Leydig cells (95%). A very small amount of testosterone is produced by adrenals (5%). The classic effects of testosterone include:
 androgen effects—the growth and development of sex organs, expression of secondary sexual features (hair growth on the face, body, limbs, as well as bald patches and baldness formation), erectile function;
 psychophysiological—libido, the formation of stereotypes of sexual behavior (aggressive, warlike behavior), mood, psycho-stimulating effect;
 reproductive—maintenance of spermatogenesis;
 anabolic—maintaining muscle mass (including myocardiocytes), stimulation of the synthesis of organ-specific proteins in kidneys, liver, sebaceous and sweat glands, maintaining bone density;
 antigonadotropic—suppression of gonadotropins secretion;

hematopoietic—stimulation of erythropoietin generating in the kidneys, stimulation of erythropoiesis in the bone marrow.

Common symptoms of androgen deficiency are disorders of sexual function (decreased libido, erectile, orgasm, ejaculation dysfunction, decreased fertility of ejaculate) and vegetative-vascular disorders (hot flashes, "tides", blood pressure fluctuations, cardialgia, feeling of short of breath), psycho-emotional disorders (irritability, decreased overall health and performance, decreased memory and attention, insomnia, depression), somatic disorders (reduction of muscle mass and strength, increase of adipose tissue amount, bone loss, gynecomastia, visceral obesity, thinning of the skin).

In recent years the pathophysiological mechanisms of androgen impact on erections have been studied. Biochemical studies data show that nitric oxide synthase is an androgen-dependent enzyme; in case of hypogonadism this enzyme deficiency leads to reduction of the synthesis and release of nitric oxide from the vascular endothelium of the corpora cavernosa and, therefore, to inadequate vasodilation due to a deficiency of cyclic guanosine monophosphate (cGMP) in the cavernous tissue.

In several studies it was shown that a decrease of testosterone concentration results in increased deposition of fat cells in the corpora cavernous which causes a degeneration of the smooth muscle cells which results in poor elasticity of cavernous tissue with formation of venous cavernous erectile insufficiency.

Kalinichenko S. Y. summarized data on the effect of androgen deficiency on erectile function:
  Reduction of relaxation of smooth muscle cells of the cavernous tissue;
  Decrease of nitric oxide production;
  Increased apoptosis of smooth muscle cells;
  Increased number of fat cells.
  However, testosterone deficiency does not always affect the mechanism of erection, but it is a pathogenic factor in libido reduction. Numerous studies of the effects of testosterone on the individual components of the copulative cycle showed that the most significant positive correlation was found between its concentration in blood and sexual desire (Jordan W. et al. 1998, Clopper, 1993). It is assumed that androgens increase desire by increasing the sensitivity of certain centers in the limbic system and hypothalamus, as well as by increasing overall activity and vitality of the body due to the stimulating effect of androgens on metabolism. This is confirmed by the fact that testosterone preparations are the most effective drugs to increase libido and stimulate the orgasmic experiences intensity.
  A lack of androgens leads to a decrease of sexual interest and activity. Effect on erectile function is more complicated (Kwan et al., 1983). Therefore, an erection could be observed over the years (Heim, 1981) after castration. Similarly, the gradual recovery of male sexual behavior in case of chronic androgen deficiency does not immediately occur under the influence of testosterone replacement therapy.
  Prolactin is a hormone involved in the growth of the prostate. Prolactin (PRL) is necessary to maintain maximal steroidogenic activity of Leydig cells in the presence of luteinizing hormone (LH); it increases the number of receptors for LH.
  Under physiological conditions, stimulation of PRL release occurs during sleep, stress, physical activity, receiving protein foods, hypoglycemia. PRL is often called a stress hormone, although the effect of mental and psychological stress on its release is not clearly demonstrated. Pathological hyperprolactinemia may be a manifestation of independent hypothalamic pituitary disease or as well a syndrome in the structure of various endocrinopathies, somatogenic and neuropsychiatric disorders (acromegaly, primary hypothyroidism, chronic renal failure, chronic prostatitis, hepatic cirrhosis).

For men, symptoms of hyperprolactinemia include reduced or absent libido and potency, reduction of secondary sexual features, infertility due to oligospermia and gynecomastia.

Chronic hyperprolactinemia in males is associated with inhibited secretion of gonadotropin-releasing hormone (GnRH), and hence of gonadotropic secretion, resulting in reduced total testosterone in serum.

It is supposed that direct depletion of dopamine (DA) in dopaminergic neurons may play a major role in the male copulation behavior, especially in reducing libido, concomitant with hyperprolactinemia.

DHEAS (dehydroepiandrosterone sulfate) is a secondary source of testosterone in men, produced primarily by the adrenal glands. DHEAS has relatively weak androgenic activity which for non-sulfonated hormone is about 10% of the testosterone level. However, its biological activity is enhanced by the relatively high concentration of serum—a hundred times superior to testosterone—as well as due to the weak affinity for steroid-binding β-globulin. This hormone is a precursor of both estrogen and testosterone.

DHEAS (and DHEA) are present in the tissues of the brain and are regarded as a neurosteroid involved in the regulation of behavior and psychophysiological reactions (stress reactions, intelligence, memory, attention, sleep). Decrease of circulating levels of DHEA and, accordingly, the ratio of DHEA/cortisol is associated with the CNS disorders such as depression, memory disorders, chronic fatigue syndrome, decreased libido, Alzheimer's disease.

By the age of 50, DHEA levels are reduced by 30% compared with those of men of the age of 30. It is widely believed that the decrease of DHEAS occurs in parallel with the decrease of well-being, and that exogenous DHEA substitution leads to an improvement in quality of life parameters.

Appendix 5—Hospital Anxiety and Depression Scale (HADS)

In clinical practice HADS scale is used to identify and assess the severity of anxiety—depressive disorders in screening studies, as well as to assess the effectiveness of psycho corrective therapy. Scale is filled in by the patient alone within 15-20 min.

HADS contains 14 symptoms and consists of two sub-scales—anxiety (A), and depression (D). Anxiety assessment includes odd items; depression—even ones. Each parameter corresponds to four choices, reflecting its presence and severity.

The invention claimed is:

1. A method of restoring male sex drive, comprising the steps of:
  providing L-arginine, pollen, male bee brood, a zinc compound, vitamin $B_6$, and horny goat weed,
  preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, and 20 to 150 mg of icariin in said horny goat weed, and
  administering one said dose daily.

2. A method of restoring male sex drive, comprising the steps of:
  providing L-arginine, pollen, male bee brood, a zinc compound, vitamin $B_6$, and *ginseng* root,
  preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, and 5 to 20 mg of saponins in said *ginseng* root, and administering one said dose daily.

3. A method of restoring male sex drive, comprising the steps of:
providing L-arginine, pollen, male bee brood, a zinc compound, vitamin $B_6$, and *Leuzea* or *Serratula coronata*,
preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, and 0.1 to 30 mg of ecdysteroids in said *Leuzea* or *Serratula coronata*, and
administering one said dose daily.

4. A method of restoring male sex drive, comprising the steps of:
providing L-arginine, pollen, male bee brood, a zinc compound, vitamin $B_6$, *ginseng* root, *Leuzea* or *Serratula coronata*,
preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, 5 to 20 mg of saponins in said *ginseng* root, and 0.1 to 30 mg of ecdysteroids in said *Leuzea* or *Serratula coronata*, and
administering one said dose daily.

5. A method of restoring male sex drive, comprising the steps of:
providing L-arginine, pollen, male bee brood, a zinc compound, vitamin $B_6$, horny goat weed, *ginseng* root, and *Leuzea* or *Serratula coronata*,
preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, 20 to 150 mg of icariin in said horny goat weed, 5 to 20 mg of saponins in said *ginseng* root, and 0.1 to 30 mg of ecdysteroids in said *Leuzea* or *Serratula coronata*, and
administering one said dose daily.

6. A method of restoring male sex drive, comprising the steps of:
providing L-arginine, pollen, male bee brood, a zinc compound, vitamin $B_6$, horny goat weed, and *ginseng* root,
preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, 20 to 150 mg of icariin in said horny goat weed, and 5 to 20 mg of saponins in said *ginseng* root, and
administering one said dose daily.

7. A method of restoring male sex drive, comprising the steps of:
providing L-arginine, pollen, male bee brood, a zinc compound, vitamin $B_6$, horny goat weed, and *Leuzea* or *Serratula coronata*,
preparing a composition of said ingredients, each dose of said composition comprising 300 to 1000 mg of L-arginine, 0.3 to 3 mg of vitamin $B_6$, 40 to 100 mg of rutin in said pollen, 0.4 to 1 mg of decenic acids in said male bee brood, 6 to 60 mg of zinc in said zinc compound, 20 to 150 mg of icariin in said horny goat weed, and 0.1 to 30 mg of ecdysteroids in said *Leuzea* or *Serratula coronata*, and
administering one said dose daily.

\* \* \* \* \*